(12) United States Patent
Takagi

(10) Patent No.: US 12,290,392 B2
(45) Date of Patent: May 6, 2025

(54) IMAGE PROCESSING APPARATUS AND STORAGE MEDIUM

(71) Applicant: Konica Minolta, Inc., Tokyo (JP)

(72) Inventor: Tatsuya Takagi, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 349 days.

(21) Appl. No.: 17/807,528

(22) Filed: Jun. 17, 2022

(65) Prior Publication Data

US 2022/0313195 A1 Oct. 6, 2022

Related U.S. Application Data

(63) Continuation of application No. 16/786,051, filed on Feb. 10, 2020, now Pat. No. 11,399,793.

(30) Foreign Application Priority Data

Feb. 21, 2019 (JP) .................................. 2019-029110

(51) Int. Cl.
*A61B 6/00* (2024.01)
*G16H 30/00* (2018.01)

(52) U.S. Cl.
CPC .......... *A61B 6/5217* (2013.01); *A61B 6/5294* (2013.01); *A61B 6/563* (2013.01); *G16H 30/00* (2018.01)

(58) Field of Classification Search
CPC .............................. A61B 6/5217; A61B 6/563
See application file for complete search history.

(56) References Cited

U.S. PATENT DOCUMENTS

| 6,422,751 | B1 | 7/2002 | Aufrichtig et al. |
| 6,934,362 | B2 | 8/2005 | Scheuering |
| 8,300,905 | B2 | 10/2012 | Jabri |
| 8,538,776 | B2 | 9/2013 | Reiner |

(Continued)

FOREIGN PATENT DOCUMENTS

| JP | 2009-142497 A | 7/2009 |
| WO | 2009142166 A1 | 11/2009 |

OTHER PUBLICATIONS

Nachabe, Rami et al. "Radiation Dose and Image Quality Comparison during Spine Surgery with Two Different, Intraoperative 3D Imaging Navigation Systems." Journal of applied clinical medical physics 20.2 (2019): 136-145. (Year: 2019).*

(Continued)

*Primary Examiner* — John R Wallace
(74) *Attorney, Agent, or Firm* — LUCAS & MERCANTI, LLP

(57) ABSTRACT

An image processing apparatus includes a hardware processor. The hardware processor estimates a body thickness and an irradiation field region of a subject based on a radiograph obtained by radiographing the subject. Further, the hardware processor calculates a distance from a focus of a radiation source to a radiation entrance point based on the body thickness. Still further, the hardware processor calculates an irradiation field size based on the irradiation field region. Yet further, the hardware processor calculates an exposure dose based on the distance, the irradiation field size, and an imaging condition used in radiographing the subject.

8 Claims, 2 Drawing Sheets

(56) References Cited

U.S. PATENT DOCUMENTS

| | | |
|---|---|---|
| 10,029,121 B2 * | 7/2018 | Li .......................... A61B 5/055 |
| 10,231,688 B2 | 3/2019 | Naito et al. |
| 2005/0002489 A1 | 1/2005 | Scheuering |
| 2007/0116348 A1 | 5/2007 | Jabri |
| 2008/0103834 A1 | 5/2008 | Reiner |
| 2016/0089104 A1 | 3/2016 | Naito et al. |
| 2018/0049713 A1 * | 2/2018 | Semba ................. A61B 6/5294 |
| 2020/0268338 A1 | 8/2020 | Takagi |
| 2021/0133979 A1 * | 5/2021 | Takahashi .............. G16H 50/20 |

OTHER PUBLICATIONS

JPO, Office Action for the corresponding Japanese patent application No. 2019-029110, dated Apr. 19, 2022, with English translation.

Hiroki Shimazaki et al., "Estimated equation of Patient Dose in Diagnostic Radiology," Japanese Journal of Medical Physics, Dec. 1999, pp. 209-217, vol. 19, No. 4, Japan (with English abstract).

* cited by examiner

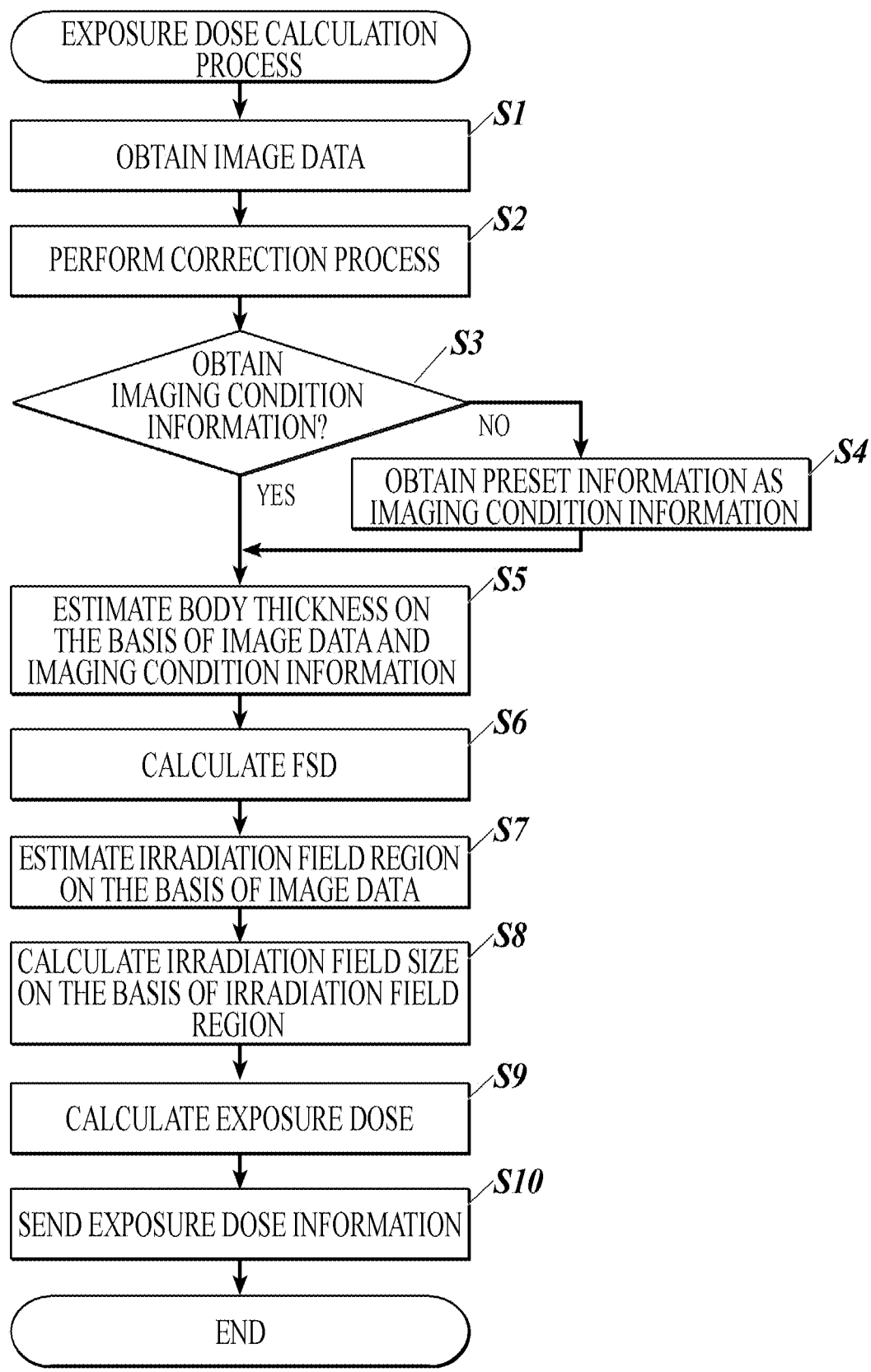

IMAGE PROCESSING APPARATUS AND STORAGE MEDIUM

CROSS-REFERENCE TO RELATED APPLICATIONS

This application is a continuation of U.S. patent application Ser. No. 16/786,051 filed Feb. 10, 2020, which, in turn, claims priority of Japanese Patent Application No. 2019-029110 filed on Feb. 21, 2019, and both application are incorporated herein by reference in their entirety.

BACKGROUND

Technological Field

The present disclosure relates to an image processing apparatus and a storage medium.

Description of the Related Art

An equation for estimating exposure doses of patients with which exposure doses (entrance surface doses) of patients can be easily obtained in any medical facility is disclosed in the following literature: Hiroki SHIMAZAKI and seven other persons, "Estimated equation of Patient dose in Diagnostic radiology," *Japanese Journal of Medical Physics*, vol. 19, no. 4, pp. 209-217. The equation for estimating exposure doses of patients has been made by adding a correction factor to an approximate equation that expresses X-ray output of X-ray apparatuses.

SUMMARY

However, the abovementioned equation for estimating exposure doses of patients uses fixed values as values of the body thickness and the irradiation field size that are necessary for determining a backscatter factor. Hence, accuracy of exposure doses of patients calculated by the above equation is low.

The present invention has been conceived in view of the above problems, and objects thereof include providing an image processing apparatus and a storage medium for easily and accurately calculating exposure doses of subjects.

In order to achieve at least one of the abovementioned objects, according to a first aspect of the present invention, there is provided an image processing apparatus including a hardware processor that:
 estimates a body thickness and an irradiation field region of a subject based on a radiograph obtained by radiographing the subject;
 calculates a distance from a focus of a radiation source to a radiation entrance point based on the estimated body thickness;
 calculates an irradiation field size based on the estimated irradiation field region; and
 calculates an exposure dose based on the calculated distance, the calculated irradiation field size, and an imaging condition used in radiographing the subject.

According to a second aspect of the present invention, there is provided a non-transitory computer-readable storage medium storing a program that causes a computer to:
 estimate a body thickness and an irradiation field region of a subject based on a radiograph obtained by radiographing the subject;
 calculate a distance from a focus of a radiation source to a radiation entrance point based on the estimated body thickness;
 calculate an irradiation field size based on the estimated irradiation field region; and
 calculate an exposure dose based on the calculated distance, the calculated irradiation field size, and an imaging condition used in radiographing the subject.

BRIEF DESCRIPTION OF THE DRAWINGS

The objects, advantages, and features provided by one or more embodiments of the present invention will become more fully understood from the detailed description given hereinbelow and the appended drawings that are given by way of illustration only, and thus are not intended as a definition of the limits of the present invention, wherein:

FIG. 4 is a flowchart of an exposure dose calculation process that is performed by the console shown in FIG. 3.

DETAILED DESCRIPTION OF EMBODIMENTS

Hereinafter, embodiments of the present invention will be described in detail with reference to FIG. 1 to FIG. 4. However, the scope of the present invention is not limited to the following embodiments, and it is needless to say that the present invention can be appropriately modified within the scope of the present invention.

Figure 1:
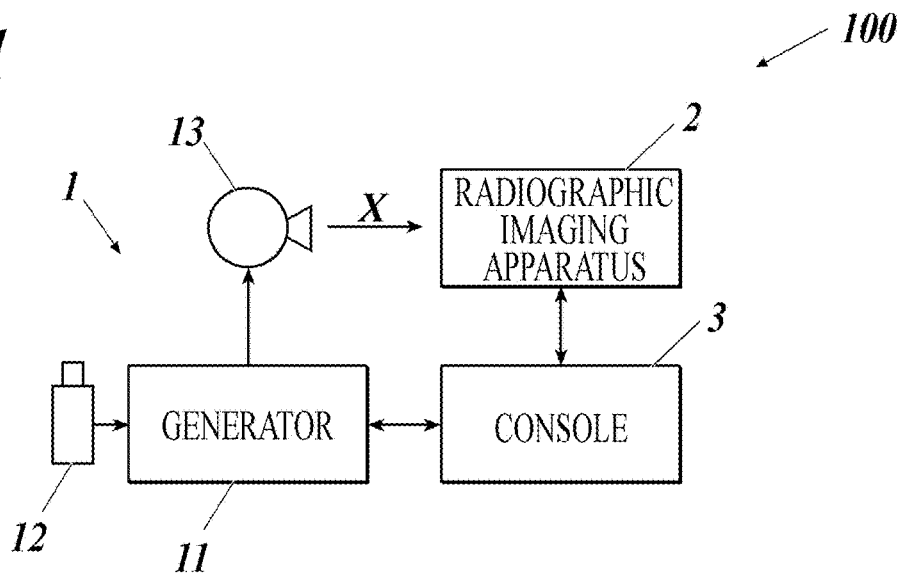
FIG. 1 is a block diagram showing configuration of a radiographic imaging system according to an embodiment (s)

Although detailed description of subjects to be photographed is omitted, the present invention can be used to photograph any part of human body. In addition, the subjects are not limited to people but include animals Radiographic Imaging System First, configuration of a radiographic imaging system according to an embodiment(s) will be described. FIG. 1 is a block diagram showing configuration of a radiographic imaging system 100.

As shown in FIG. 1, the radiographic imaging system 100 of this embodiment includes an irradiation apparatus 1, a radiographic imaging apparatus 2, and a console 3 that functions as an image processing apparatus.

The radiographic imaging system 100 can be connected to a radiology information system (RIS), a picture archiving and communication system (PACS), and so forth (all not shown).

The irradiation apparatus 1 can be communicably connected to the console 3 by wire or wirelessly.

The irradiation apparatus 1 includes a generator 11, an exposure switch 12, and a radiation source 13.

The generator 11 applies a voltage in accordance with preset imaging conditions (tube voltage, tube current, irradiation time (mAs value), etc.) to the radiation source 13 in response to the exposure switch 12 being operated. Further, the generator 11 can send, to the console 3, imaging condition information indicating the imaging conditions used in radiographing a subject.

The radiation source 13 (light bulb) includes a rotating anode and a filament (both not shown). When the generator 11 applies the voltage to the radiation source 13, the filament emits an electron beam corresponding to the applied voltage to the rotating anode, and the rotating anode generates radiation X (X-rays, etc.) of a dose corresponding to the intensity of the electron beam.

Although FIG. 1 shows the components 11 to 13 that separate from one another, they may be unitized.

Further, although FIG. 1 shows the exposure switch 12 connected to the generator 11, the exposure switch 12 may be provided in/on another apparatus (e.g. a not-shown console).

The irradiation apparatus 1 may be installed in an imaging room, or combined with a nursing cart or the like to be movable.

The radiographic imaging apparatus 2 is communicably connected to the console 3 by wire or wirelessly.

The radiographic imaging apparatus 2 generates image data of a subject by receiving the radiation X via the subject from the irradiation apparatus 1.

The radiographic imaging apparatus 2 will be described in detail later.

The console 3 is constituted of a PC, a portable terminal, or a dedicated apparatus, and is communicably connected to the irradiation apparatus 1, the radiographic imaging apparatus 2, and/or the like by wire or wirelessly.

The console 3 can set imaging conditions, an imaging target part(s) (part(s) of a subject to be photographed), and so forth into the irradiation apparatus 1 and the radiographic imaging apparatus 2 (via the communication unit 32) on the basis of an imaging order from an external apparatus (RIS, etc.) or on the basis of user operations.

The console 3 will be described in detail later.

Radiographic Imaging Apparatus

Figure 2:
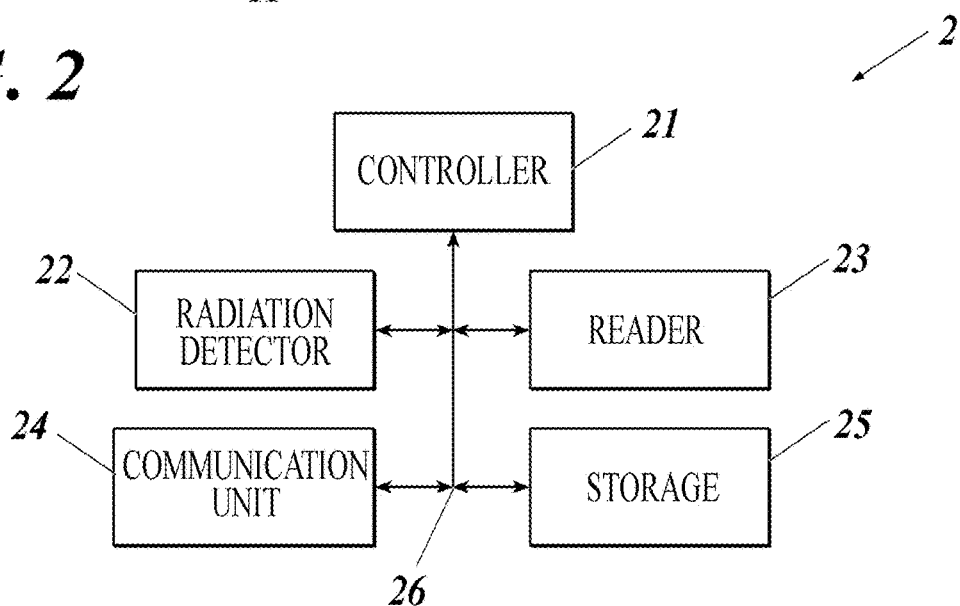
FIG. 2 is a block diagram showing configuration of a radiographic imaging apparatus included in the radiographic imaging system shown in FIG. 1.

Next, the radiographic imaging apparatus 2 included in the radiographic imaging system 100 will be described in detail. FIG. 2 is a block diagram showing configuration of the radiographic imaging apparatus 2.

As shown in FIG. 2, the radiographic imaging apparatus 2 includes a controller 21, a radiation detector 22, a reader 23, a communication unit 24, a storage 25, and a bus 26 that connects the components 21 to 25 with one another.

The controller 21 includes a central processing unit (CPU) and a random access memory (RAM). In response to control signals or the like received from external apparatuses, such as the console 3, the CPU of the controller 21 reads various programs stored in the storage 25, loads the read programs into the RAM, and performs various processes in accordance with the loaded programs, thereby centrally controlling operation of each component of the radiographic imaging apparatus 2.

The radiation detector 22 is constituted of a substrate in which pixels are arranged two-dimensionally (in a matrix). Each pixel has a radiation detection element and a switch element. The radiation detection elements generate charges corresponding to the dose of the radiation X received.

The reader 23 reads the amounts of charges discharged from the respective pixels as signal values, and generates image data from the signal values.

The communication unit 24 receives various control signals, various data, and so forth from external apparatuses, and sends various control signals, generated image data, and so forth to external apparatuses.

The storage 25 includes a nonvolatile semiconductor memory and/or a hard disk, and stores various programs that are executed by the controller 21, parameters that are required to perform processes in accordance with the programs, and so forth. The storage 25 also stores image data generated by the reader 23 and various data processed by the controller 21.

In the radiographic imaging apparatus 2 configured as described above, the radiation detector 22 accumulates, in the pixels, charges corresponding to the dose of the radiation X by receiving the radiation X in a state in which the controller 21 has turned off the switch elements. When the controller 21 turns on the switch elements, and the charges are discharged from the pixels accordingly, the reader 23 converts the amounts of the charges into signal values, and reads the signal values as image data.

The radiographic imaging apparatus 2 may be, what is called, an indirect radiographic imaging apparatus that includes a scintillator, and converts received radiation X with the scintillator into light having another wavelength, such as visible light, and generates charges corresponding to the light, into which the radiation X has been converted, or may be, what is called, a direct radiographic imaging apparatus that directly generates charges from received radiation X without a scintillator or the like.

The radiographic imaging apparatus 2 may be integrated with an imaging table (dedicated type), or may be portable (cassette type).

Console

Figure 3:
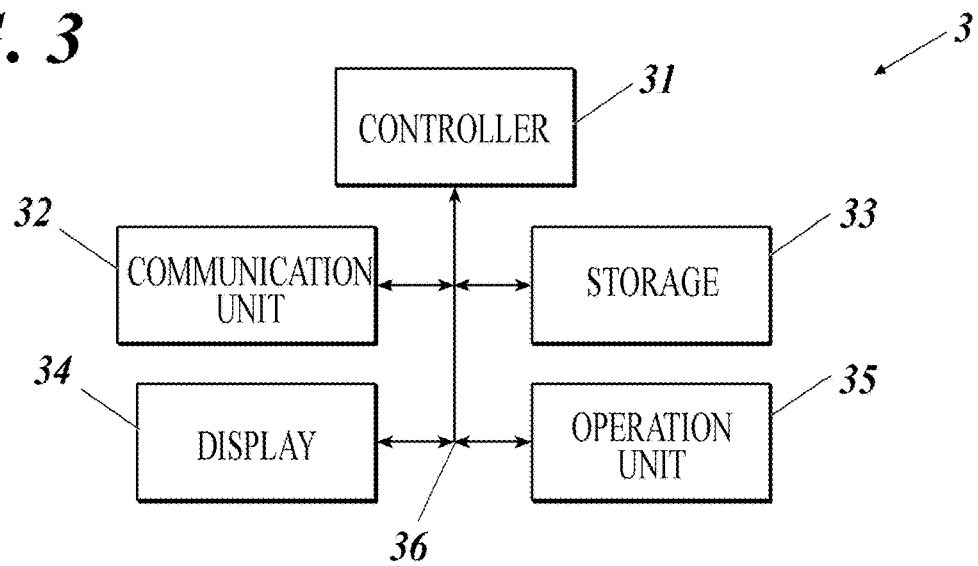
FIG. 3 is a block diagram showing configuration of a console included in the radiographic imaging system shown in FIG. 1.

Next, the console 3 included in the radiographic imaging system 100 will be described in detail. FIG. 3 is a block diagram showing configuration of the console 3.

As shown in FIG. 3, the console 3 includes a controller 31 (hardware processor), a communication unit 32, a storage 33, a display 34, an operation unit 35, and a bus 36 that connects the components 31 to 35 with one another.

The controller 31 includes a central processing unit (CPU) and a random access memory (RAM). In response to operations on/with the operation unit 35, the CPU of the controller 31 reads various programs stored in the storage 33, loads the read programs into the RAM, and performs various processes in accordance with the loaded programs, thereby centrally controlling operation of each component of the console 3.

The communication unit 32 includes a LAN adapter, a modem, and a terminal adapter (TA), and controls data sending to and data receiving from external apparatuses connected to a communication network(s).

The storage 33 includes a nonvolatile semiconductor memory and/or a hard disk, and stores various programs (including a program for an exposure dose calculation process described below) that are executed by the controller 31, parameters that are required to perform processes in accordance with the programs, and so forth. The storage 33 also stores image data received from the radiographic imaging apparatus 2 and image data processed by the controller 31.

The storage 33 also stores imaging condition information received from the irradiation apparatus 1. The storage 33 also stores alternative data to be used as imaging condition information when imaging condition information is not received (obtained) from the irradiation apparatus 1 in the exposure dose calculation process described below. The alternative data are preset, and are pieces of information associated with respective predetermined imaging techniques in radiography.

The display 34 is constituted of a monitor, such as a liquid crystal display (LCD) or a cathode ray tube (CRT), and displays instructions input from the operation unit 35, data, and so forth in accordance with instructions of display signals input from the controller 31.

The operation unit 35 includes: a keyboard including cursor keys, number input keys, and various function keys; and a pointing device, such as a mouse, and outputs, to the controller 31, instruction signals input by a user operating the keys of the keyboard or the mouse.

The operation unit 35 may have a touchscreen on the display screen of the display 34. In this case, the operation unit 35 outputs, to the controller 31, instruction signals input via the touchscreen.

Exposure Dose Calculation Process

Next, the exposure dose calculation process, which is one of the processes that are performed by the console 3, will be described in detail. FIG. 4 is a flowchart of the exposure dose calculation process that is performed by the console 3.

The controller 31 of the console 3 of this embodiment performs the exposure dose calculation process in response to satisfaction of a predetermined start condition, such as a start operation on/with the operation unit 35, a press on the exposure switch 12, or an imaging process with the irradiation apparatus 1 and the radiographic imaging apparatus 2. Examples of the exposure dose of a subject calculated in the exposure dose calculation process include the dose area product, the entrance surface dose, the effective dose, and the equivalent dose. Methods for calculating the effective dose and the equivalent dose are detailed in the following literature: Takashi MARUYAMA, Kazuo IWAI, Kanae, NISHIZAWA, Yutaka NODA and Yoshikazu KUMAMOTO, "Organ or Tissue Doses, Effective Dose and Collective Effective Dose from X-Ray Diagnostics, in Japan," *RADIOISOTOPES*, vol. 45 (1996) no. 12.

As shown in FIG. 4, first, the controller 31 obtains image data (radiograph) generated by the radiographic imaging apparatus 2 in response to the irradiation apparatus 1 irradiating a subject with radiation (Step S1).

Preferably, the console 3 (controller 31) obtains the image data by receiving the image data via the communication unit 32 by wire or wirelessly, but may obtain the image data via a medium, such as a USB memory.

In order to obtain the image data, the console 3 may send a data sending request signal to the radiographic imaging apparatus 2, thereby requesting the radiographic imaging apparatus 2 to send the image data, or may wait (repeat Step S1) until the radiographic imaging apparatus 2 sends the image data.

Next, the controller 31 performs a correction process(es), such as gain correction, offset correction, and/or defective pixel correction, on the image data obtained in Step S1 (Step S2).

Next, the controller 31 determines whether or not it has obtained imaging condition information indicating imaging conditions used in radiographing the subject from the irradiation apparatus 1 (generator 11) (Step S3).

If the controller 31 determines in Step S3 that it has obtained imaging condition information from the irradiation apparatus 1 (Step S3; YES), the controller 31 proceeds to Step S5.

If the controller 31 determines in Step S3 that it has not obtained imaging condition information from the irradiation apparatus 1 (Step S3; NO), the controller 31 obtains (a piece of) alternative data from the storage 33 as imaging condition information (Step S4) and proceeds to Step S5.

As described above, the alternative data are pieces of information associated with respective predetermined imaging techniques in radiography. The controller 31 obtains, as imaging condition information, a piece of information associated with an imaging technique specified via the operation unit 35 among the pieces of information associated with the respective imaging techniques.

Next, the controller 31 estimates the body thickness on the basis of the image data corrected in Step S2 and the imaging condition information obtained in Step S3 or Step S4 (Step S5). As a method for estimating the body thickness, for example, a method disclosed in JP 2016-067712 A may be used. The controller 31 may estimate the body thickness on the basis of only the image data corrected in Step S2 without taking the imaging condition information obtained in Step S4 into account. As a method for estimating the body thickness on the basis of only the image data, for example, a method disclosed in JP 2015-167613 A may be used.

Next, the controller 31 calculates the distance from the focus of the radiation source 13 to a radiation entrance point (hereinafter, referred to as FSD (Focus (to) Surface Distance)) on the basis of the body thickness estimated in Step S5 (Step S6). More specifically, the controller 31 calculates the FSD by subtracting the body thickness from a radiation-source-to-detector distance (hereinafter referred to as SID (Source to Image Distance)), which is included in the imaging condition information.

Next, the controller 31 estimates the irradiation field region on the basis of the image data corrected in Step S2 (Step S7). As a method for estimating the irradiation field region, for example, a method disclosed in JP 5,998,903 B may be used.

Next, the controller 31 calculates the irradiation field size (e.g. the length of the irradiation field region in the horizontal direction and the length of the irradiation field region in the vertical direction) on the basis of the irradiation field region estimated in Step S7 (Step S8).

Next, the controller 31 calculates the exposure dose (entrance surface dose and dose area product (DAP value) in this embodiment) on the basis of the FSD calculated in Step S6, the irradiation field size calculated in Step S8, and the imaging conditions (kV, mAs, filter type) included in the imaging condition information (Step S9). More specifically, the controller 31 calculates the entrance surface dose by substituting a correction factor, which is determined by the FSD, the irradiation field size, and the imaging conditions (kV, mAs, filter type), into the NDD formula (simple surface dose conversion formula), and also calculates the dose area product (DAP value). As a method for calculating the dose area product (DAP value), for example, a method disclosed in the following literature may be used: Hajime SAKAMOTO and five other persons, "A Study of Patient's Dose Control Using an Area Exposure Product Meter," *Japanese Journal of Radiological Technology*, vol. 56, no. 10.

Next, the controller 31 sends data (exposure dose information) of the entrance surface dose and the dose area product calculated in Step S9 to the radiology information system (RIS) (Step S10) and ends the exposure dose calculation process.

When sending the exposure dose information, the controller 31 may also send body thickness information indicating the body thickness estimated in Step S5. This allows the radiology information system (RIS) to manage exposure doses of subjects (patients) by body type (e.g. slender/ectomorph, standard/mesomorph, plump/endomorph, etc.). As a result, for example, the diagnostic reference levels (DRLs) can be calculated with only people of the standard body type targeted.

When sending the exposure dose information, the controller 31 may also send index information (e.g. EI value, S value, etc.) representing the quality of the radiograph. This allows the radiology information system (RIS) to identify values of exposure doses for the optimum quality of radiographs.

When sending the exposure dose information, the controller 31 may also send failure/success information indicating whether or not the radiograph is a failed image. This allows the radiology information system (RIS) to manage successful image data and failed image data separately from one another.

As described above, the controller 31 of the console 3 estimates the body thickness and the irradiation field region of a subject on the basis of image data (radiograph) obtained by radiographing the subject, calculates the distance (FSD) from the focus of a radiation source to a radiation entrance point on the basis of the estimated body thickness, calculates the irradiation field size on the basis of the estimated irradiation field region, and calculates the exposure dose on the basis of the calculated FSD, the calculated irradiation field size, and an imaging condition(s) used in radiographing the subject.

Thus, the exposure dose is calculated by using the FSD and the irradiation field size that are actually calculated from the image data (radiograph). Hence, the exposure dose can be easily and accurately calculated.

Further, the controller 31 of the console 3 estimates the body thickness by taking the imaging condition used in radiographing the subject into account. Hence, an estimation error of the body thickness can be reduced.

Further, in response to not obtaining imaging condition information indicating the imaging condition from the irradiation apparatus 1, the controller 31 obtains alternative data (preset information) as the imaging condition information. Thus, the exposure dose can be calculated by using the alternative data.

Hence, even when the console 3 and the irradiation apparatus 1 are not in cooperation with one another, the exposure dose can be calculated.

Further, the alternative data includes pieces of information associated with respective predetermined imaging techniques in radiography, and the controller 31 of the console 3 obtains, as the imaging condition information, a piece of the information associated with an imaging technique specified on the basis of a user operation. Hence, even when the console 3 and the irradiation apparatus 1 are not in cooperation with one another, the exposure dose can be calculated accurately.

Those described in the above embodiment are preferred examples of the present invention, and hence not intended to limit the present invention.

For example, although in the above embodiment, both the entrance surface dose and the dose area product (DAP value) are calculated as the exposure dose in the exposure dose calculation process, only one of the entrance surface dose and the dose area product (DAP value) may be calculated.

Further, for example, in the above embodiment, the irradiation apparatus 1 may further include an area dosimeter (measurer), and the controller 31 of the console 3 may determine whether or not a difference between the exposure dose measured by the area dosimeter and the exposure dose calculated in the above exposure dose calculation process is equal to or greater than a predetermined threshold, and in response to determining that the difference is equal to or greater than the predetermined threshold, causes, for example, the display 34 (notifying unit) to notify a user that the difference is equal to or greater than the predetermined threshold.

Further, for example, in the above embodiment, the controller 31 of the console 3 may calculate the exposure dose on the basis of a signal value of a hollow hole part of the radiograph (image data), determine whether or not a difference between (i) the exposure dose calculated on the basis of the signal value of the hollow hole part and (ii) the exposure dose calculated in the above exposure dose calculation process is equal to or greater than a predetermined threshold, and in response to determining that the difference is equal to or greater than the predetermined threshold, causes, for example, the display 34 to notify a user that the difference is equal to or greater than the predetermined threshold.

Further, for example, in the above embodiment, the controller 31 of the console 3 may specify the imaging condition information, which is used in calculating the exposure dose in the above exposure dose calculation process, for example, via the operation unit 35. In this case, the imaging condition information can be corrected, for example, after the exposure dose is calculated, so that the exposure dose can be recalculated.

Further, for example, although in the above description, a hard disk and a nonvolatile semiconductor memory are disclosed as examples of a computer-readable storage medium storing the program(s) of the present invention, the computer-readable storage medium is not limited to these. As the computer-readable storage medium, a portable storage medium, such as a CD-ROM, may also be used. Also, as a medium that provides, via a communication line, data of the program(s) of the present invention, a carrier wave may be used.

The detailed configuration and detailed operation of each apparatus or the like of the radiographic imaging system can also be appropriately modified within the scope of the present invention.

Although some embodiments of the present invention have been described and illustrated in detail, the disclosed embodiments are made for purposes of not limitation but illustration and example only. The scope of the present invention should be interpreted by terms of the appended claims.

What is claimed is:

1. A combination including an image processing apparatus and a radiology information system that manages a radiograph obtained by radiographing a subject,
    the image processing apparatus configured to estimate a body thickness and an irradiation field region of the subject based on the radiograph, calculate a focus to surface distance (FSD) from a radiation focus to a radiation entrance point based on the estimated body thickness, and calculate an exposure dose based on the calculated FSD, a result of the estimated irradiation field region, and imaging condition information, and
    the radiology information system comprising a hardware processor that
    receives information output from the image processing apparatus, the information including body thickness information indicating the body thickness and exposure dose information indicating the exposure dose,
    manages the body thickness information and the exposure dose information, and
    calculates a diagnostic reference level based on the body thickness information and the exposure dose information.

2. The combination including the image processing apparatus and the radiology information system according to claim 1, wherein the hardware processor manages, based on the body thickness information, the exposure dose by a body type of the subject.

3. The combination including the image processing apparatus and the radiology information system according to claim 1, wherein the hardware processor manages index information representing a quality of the radiograph together with the body thickness information and the exposure dose information.

4. The combination including the image processing apparatus and the radiology information system according to claim 3, wherein the index information includes at least one of an EI value and an S value.

5. The combination including the image processing apparatus and the radiology information system according to claim 1, wherein the hardware processor manages the radiograph based on the radiograph being a successful image or a failed image.

6. The combination including the image processing apparatus and the radiology information system according to claim 1, wherein the image processing apparatus calculates the FSD by subtracting the estimated body thickness from a radiation-source-to-detector distance used during the radiographing, the radiation-source-to-detector distance being included in the imaging condition information.

7. The combination including the image processing apparatus and the radiology information system according to claim 1, wherein the image processing apparatus obtains preset information as the imaging condition information when actual imaging condition information used during the radiographing is not obtained.

8. A system comprising:
   an image processing apparatus that estimates a body thickness and an irradiation field region of a subject based on a radiograph, calculates a distance (FSD) from a radiation focus to a radiation entrance point based on the estimated body thickness, and calculates an exposure dose based on the calculated FSD, a result of the estimated irradiation field region, and imaging conditions used in radiographing the subject;
   an external apparatus that is external and connected to the image processing apparatus; and
   a hardware processor that
      receives information output from the image processing apparatus, the information including body thickness information indicating the body thickness and exposure dose information indicating the exposure dose,
      manages the body thickness information and the exposure dose information, and
      calculates a diagnostic reference level based on the body thickness information and the exposure dose information.

\* \* \* \* \*